United States Patent [19]
Gordon

[11] 4,391,710
[45] Jul. 5, 1983

[54] CYTOCENTRIFUGE

[75] Inventor: Alan J. Gordon, Liverpool, England

[73] Assignee: Shandon Southern Products Limited, Runcorn, England

[21] Appl. No.: 289,374

[22] Filed: Aug. 3, 1981

[30] Foreign Application Priority Data

Sep. 15, 1980 [GB] United Kingdom ................ 8029732

[51] Int. Cl.$^3$ ............................................ B01D 33/22
[52] U.S. Cl. .................................... 210/361; 422/101
[58] Field of Search ............ 210/781, 782, 361, 512.1; 233/2; 422/72, 73, 101, 102

[56] References Cited

U.S. PATENT DOCUMENTS

| | | | |
|---|---|---|---|
| 2,854,143 | 9/1958 | Novak | 233/2 |
| 3,300,051 | 1/1967 | Mitchell | 210/361 |
| 3,953,172 | 4/1976 | Shapiro et al. | 422/72 |
| 4,244,694 | 1/1981 | Farina et al. | 422/72 |

*Primary Examiner*—Ivars C. Cintins
*Attorney, Agent, or Firm*—Kurt Kelman

[57] ABSTRACT

A cytocentrifuge especially suitable for centrifugation of materials requiring handling under conditions of containment is characterized by a plurality of holders each adapted to retain an individual sample chamber in juxtaposition to a receiving surface with interposed filter/seal and removable as a unit from the rotating carrier of the machine. The holder is preferably adapted to be supported tiltingly by the carrier so as only under centrifugal force to permit a sample to contact the receiving surface and while this is perpendicular to the centrifugal load on the sample. The carrier is preferably an apertured plate removable from a drive hub for cleansing and sterilization, and the drive hub forms part of a sealable head assembly of containment bowl and removable cover, the head assembly being removable as a unit for loading/unloading under containment conditions.

13 Claims, 4 Drawing Figures

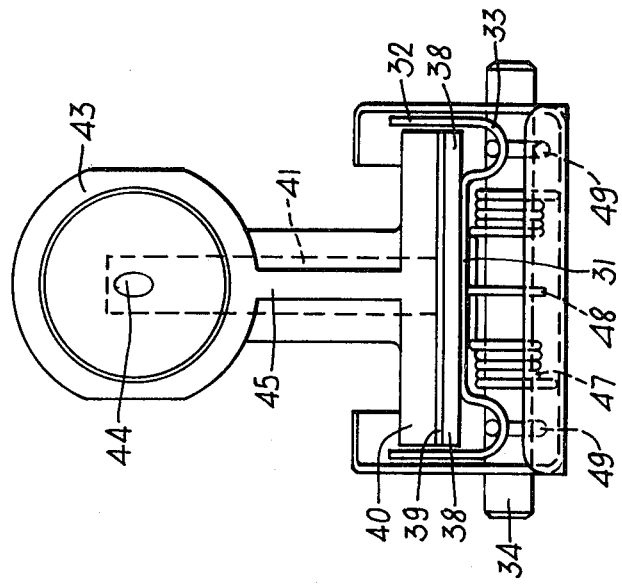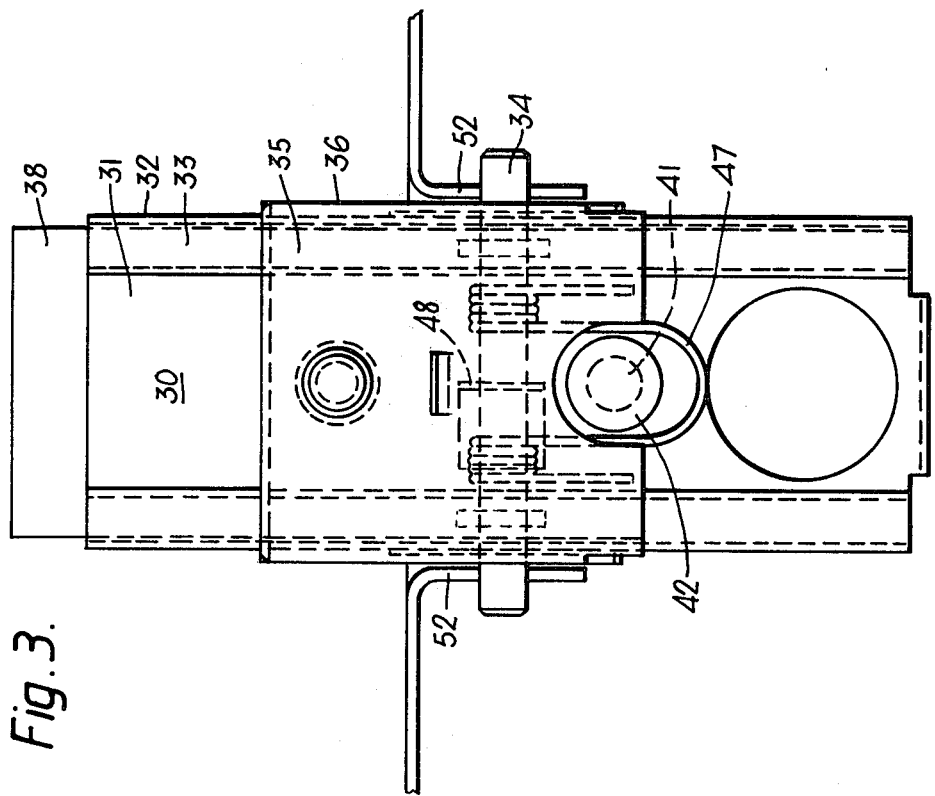

CYTOCENTRIFUGE

BACKGROUND OF PRIOR ART

This invention relates to cytocentrifuges, that is to say, centrifuge machines for the centrifugation of small samples of, e.g., body fluids such as cerebrospinal fluid, for separating and depositing cells and other solids suspended in the fluid in a manner permitting examination thereof by microscopy. Such cytocentrifuges are routinely used in hospital and other laboratories in diagnostic and investigative procedures and need therefore to be capable of being quickly set up to effect centrifugation of a first set of samples and of being quickly and easily reloaded for the centrifugation of second and subsequent sets of samples. Moreover as many of the materials that have to be subjected to centrifugation by such a machine may be toxic or release toxic or noxious matter during centrifugation, the construction of the machine must lend itself to loading and unloading of samples in a suitable containment zone such as a fume cupboard, and also allow of easy cleansing and sterilization of those components liable to come into contact with samples or other released matter.

Cytocentrifuges currently in use provide a sample chamber of generally tubular form that during the centrifugation operation is aligned with a radius to the vertical axis of rotation and has its outer end closed by a microscope slide or the like providing a surface for receiving deposited cells and other solids, the junction between the chamber and this receiving surface being sealed by an annulus of absorbent material such as filter card that both prevents leakage of the liquid component of the sample and absorbs this liquid so as to leave the cells and other deposited solids as a dry layer on the receiving surface at the conclusion of the centrifugation operation.

Various arrangements are in use or have been proposed for effecting the required conjunction of the sample chamber, receiving surface and filter/seal but typically these involve an assembly operation to be carried out upon or in conjunction with the rotating carrier of the centrifuge and that typically carries a number of symmetrically disposed sample chambers with associated receiving surfaces and filter/seals. These arrangements are generally tedious and inconvenient to manipulate, especially when the material being centrifuged, and any centrifuge components coming into contact therewith, must all be handled under conditions of containment to prevent escape of toxic or noxious matter.

One object of the present invention is therefore to provide a cytocentrifuge that avoids these disadvantages of the prior art constructions and that lends itself to rapid loading, unloading and reloading with samples, especially under conditions of containment, to allow of a high rate of utilization of the machine.

A further object of the invention, achieved in preferred embodiments, is to provide a cytocentrifuge capable of meeting the anticipated requirement for such machines to provide sealed containment of the carrier and sample chambers during operation and permitting loading and unloading to be accomplished in a containment zone, preferably without the need for the machine itself to be located in such a zone.

THE INVENTION

In accordance with the present invention, a cytocentrifuge is characterized by a plurality of holders each adapted to retain an individual sample chamber in juxtaposition to a receiving surface with interposed filter/seal and being removable as a unit from the rotating carrier of the machine.

Thus in a cytocentrifuge in accordance with the invention, assemblies of holders with sample chambers, receiving surfaces and filter/seals may be pre-assembled in advance of utilization and may thereafter be fitted to the carrier as and when required, loaded with sample material that is then centrifuged by the machine, and thereafter be removed from the carrier for disassembly as and when desired for examination of matter deposited on the receiving surfaces, while other like assemblies are fitted to the carrier for the centrifugation of further samples. The holders and the sample chambers may be cleaned and sterilized individually or in batches in a dismantled condition as desired and as and when convenient, without prejudice to continued operation of the machine with the use of other holder/sample chamber assemblies.

In preferred embodiments of the invention, each holder comprises a channel member adapted to receive a glass or other suitable slide providing a receiving surface, overlaid by a filter card and by a correspondingly shaped end flange at an end of a tubular sample chamber, the holder further comprising clamping means adapted to engage the said end flange of the sample chamber to urge this towards the web of the holder channel member thereby to secure the assembly of sample chamber, filter card and slide in place. Preferably the holder channel member has an end stop at one end to locate the components in the required mutual relationship with one another and with the holder, the other end of the channel member being open to permit the components to be slid out of the channel member upon release of the said clamping means.

In preferred embodiments of the invention, the said clamping means comprise a rocking element pivoted to the channel member and having lugs extending over the flanges of the channel member to engage the end flange of the sample chamber, the rocking element being springloaded so as to rock in the required direction to cause said lugs to tend to move towards the web of the channel member to produce a clamping force on the end flange of the associated sample chamber. The rocking element may be formed with a fingerpiece or the like to enable it to be rocked manually against the spring force but in preferred embodiments the rocking element carries a release screw that may be manipulated first to engage the outer face of the channel member web and thereafter forcibly to rock the rocking element in the clamp-releasing direction and to hold the rocking element in a clamp-released position to facilitate assembly and disassembly of the sample chamber, filter card and slide in the holder.

In preferred embodiments the holder channel is of M-section, presenting lateral stiffening ribs along its rear or outer aspect, these ribs being recessed to provide locations for a pivot rod that extends across such ribs and through a rearwardly directed tang pressed out of the web, this pivot rod extending through side cheeks in the rocking element and carrying a hairpin spring acting respectively on the rear face of the holder web and upon the rocking element to tend to rotate the latter about the pivot rod.

Preferably the lugs of the rocking element are positioned to engage the end flange of the sample chamber adjacent to a diameter of the latter so as to apply clamping force generally symmetrically with respect to the axis of the sample chamber.

The holder channel member and the rocking element are both preferably formed from stainless steel sheet as by pressing or stamping.

The sample chamber is preferably formed of plastics material and in preferred embodiments comprises a tube having one end integrally formed with a rectangular end flange, and a lateral filling orifice near its other end. The filling orifice preferably communicates with a funnel tube to facilitate introduction of sample material into the filling orifice and desirably the funnel tube is integrally formed with the sample chamber and also with lateral flanges that extend to join the end flange of the sample chamber along the longitudinal centerline of the end flange.

In accordance with a further feature of the invention, the holder is preferably adapted to be supported by the carrier of the machine in a manner permitting tilting of the holder about a horizontal axis in response to gravitational and centrifugal loads in such a manner that when the carrier is at rest a holder with assembly of sample chamber, slide and filter/seal adopts a position in which the axis of the sample chamber is inclined downwardly and inwardly of the carrier, whereas under centrifugal loads arising from rotation of the carrier, the holder tilts to a position in which the sample chamber axis is horizontal and perpendicular to the axis of rotation.

By virtue of this feature, a sample introduced into the sample chamber through the filling orifice when the respective holder is fitted to the carrier will, because of the inclination of the sample chamber, remain at the inner end of the latter, out of contact with the receiving surface and the filter/seal. Only when the carrier is rotated will the sample move into contact with the receiving surface of the slide and be capable of depositing matter on the latter. In this way the formation of a desirable uniform, single cell thickness, layer of deposited matter on the receiving surface is promoted, facilitating subsequent microscopic examination of the deposited matter. Because the holder tilts under centrifugal loads to bring the sample chamber axis perpendicular to the axis of rotation—and accordingly brings the receiving surface accurately perpendicular to the centrifugal force acting on the sample—there is no risk that the matter deposited on the receiving surface will show asymmetry of thickness or deposition about the axis of the sample chamber.

The permissible tilting of the holder relative to the carrier is determined by cooperation of the respective components. Only a small angular tilting movement is required and in the case of a sample chamber designed to accept a sample of 0.5 ml volume a total angular movement of 13 degrees has been found to be satisfactory.

In accordance with a further feature of the invention, the carrier is preferably formed as a plate with apertures to receive an appropriate number of holder/sample chamber assemblies and a central aperture to fit over a drive hub from which the carrier plate may be removed at will for cleansing and sterilization as required.

Moreover, preferably the drive hub carries a containment bowl and removable cover constituting a sealable head assembly that may be removed as a unit from the machine to permit of its being handled in a containment zone, such as a fume cupboard or the like, e.g. while being loaded and unloaded with holder/sample chamber assemblies and when the latter are being loaded with sample material.

Preferably the drive hub is formed with an internal tapered drive surface for mating with a complementarily tapered driving element on a vertical drive shaft, no locking or other coupling devices being utilised to transmit the drive to the drive hub, so as to facilitate the ready removal and replacement of the head unit.

THE DRAWINGS

An embodiment of the invention is illustrated in the accompanying drawings in which:

FIG. 3 is a fragmentary sectional elevation of part of the carrier and a holder/sample chamber assembly; and FIG. 4 is a plan section of the holder/sample chamber assembly.

DESCRIPTION OF EMBODIMENT

Figure 1:
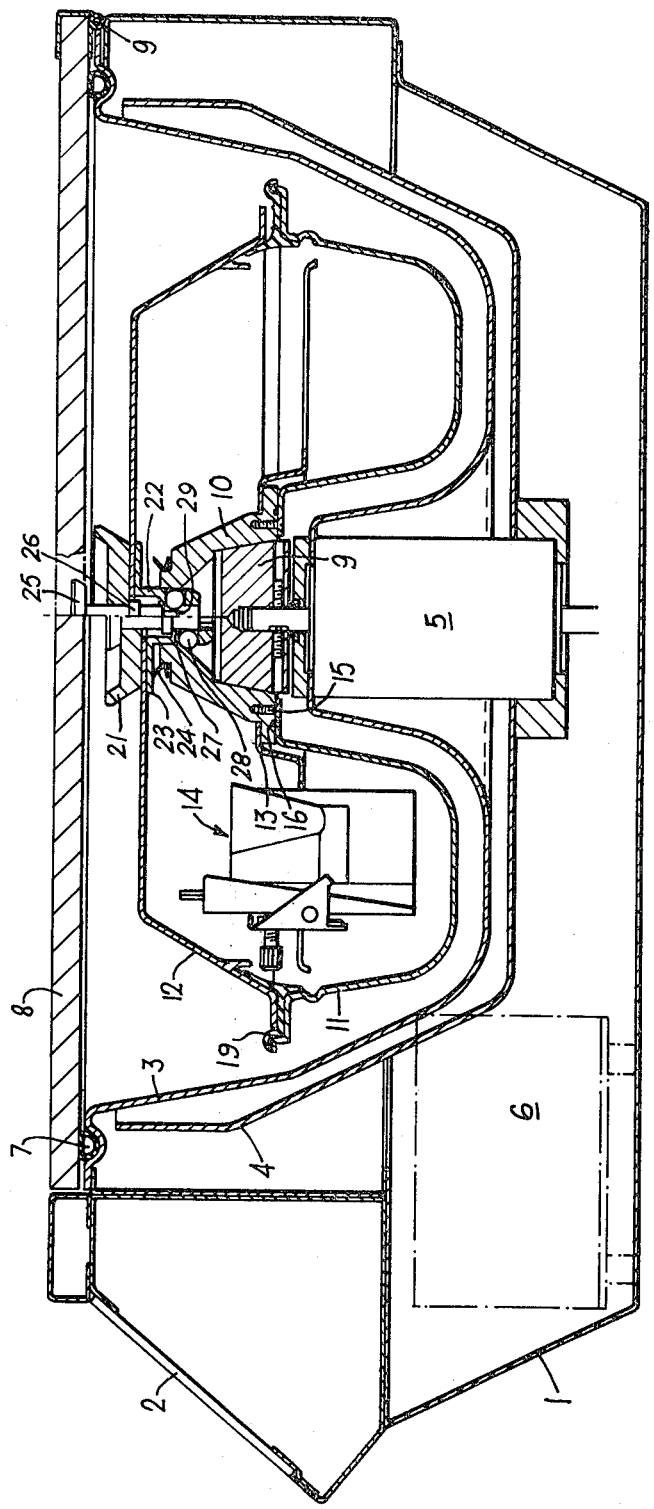
FIG. 1 is a partly schematic vertical sectional view of a cytocentrifuge embodying the invention.

The cytocentrifuge illustrated in the drawings is generally rectangular in plan view and comprises an outer casing providing a plinth 1 and external walls including a control panel 2 and supporting an inner containment bell 3 stiffened by external ribs and an outer bell 4 that in conjunction with the bell 3 provides a mounting for a vertically disposed drive motor 5 the power supply to which is controlled by suitable control gear 6 disposed within the plinth 1 and including the usual timers, safety cut-off mechanism and the like. The upper end of the inner bell 3 is formed with a seating groove for a peripheral D-ring seal 7 for cooperation with a lid 8 hinged at 9 to the outer casing.

The drive shaft of the motor 5 carries a male taper drive element 9 that cooperates with a complementary female taper on a drive hub 10 that forms part of a removable head unit comprising a bowl 11, a removable sealing cover 12 and a carrier plate 13 for a set of holder/sample chamber assemblies one of which is generally indicated at 14.

The bowl is fixed to the underside of the drive hub 10 by means of screws such as indicated at 15 and is sealed to the hub 10 by a suitable ring seal 16. Near its outer extremity the bowl 11 is formed with a peripheral groove 17 that serves to trap any liquid matter that may escape from a sample holder during centrifugation and to prevent its flowing to the periphery of the bowl where the latter is formed with a lipped peripheral flange 18 that carries a seal 19 for engagement by a peripheral flange 20 on the cover 12. As best shown in FIG. 2, the seal 19 has a limb 19a that, with the cover 12 in place, is trapped between the flanges 18 and 20, this limb of the seal having ribs 19b to be engaged and compressed by the flanges. The seal limb 19a terminates externally in a hooked portion that locates over the flange 18, and internally in a flexible web 19c that overlies the junction between the bowl and cover and is forced into sealing engagement therewith by centrifugal force during centrifugation, to prevent any escape of matter from the bowl. The cover 12 has an internal dependent rib 12a that overlies the edge of the web 19c of the seal 19 to prevent liquid matter reaching the seal edge. The left-hand side of FIG. 1 shows the cover 12 in its closed condition engaging the sealing ring 19 whereas the right-hand side of FIG. 1 shows the cover in a partly open condition.

As shown, the cover 12 is fitted centrally with an external knob 21 and an internal boss 22 having a flange 23 by which it is attached to the cover 12 and that provides a surface for cooperation with a V-ring seal 24 on the hub 10 in the closed position of the cover.

Figure 2:
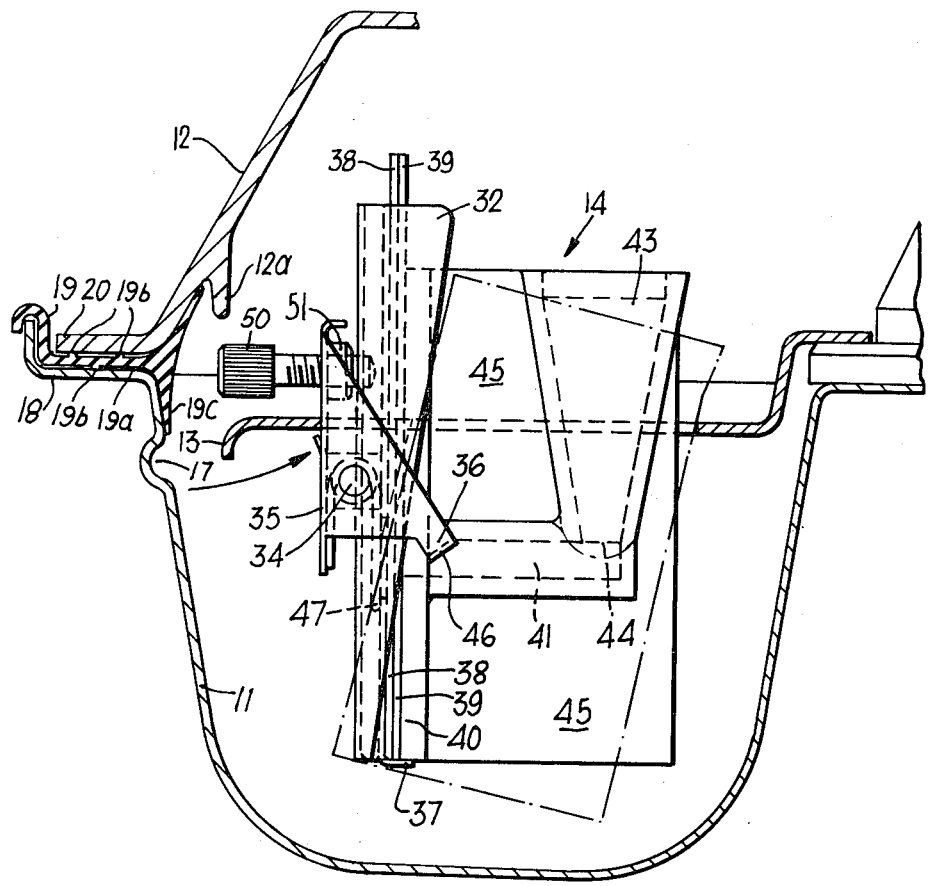
FIG. 2 is a fragmentary radial sectional view, on a larger scale than FIG. 1, of part of the removable head unit of the machine.

A locking plunger 25 extends centrally through the knob 21 and boss 22 and is movable axially between the limits determined by engagement of a rib 26 with the underside of the knob 21 (right-hand side FIG. 1) and with an internal flange 27 in the boss 22 (left-hand side of FIG. 1).

The boss 22 has captive detent balls 28 situated in lateral recesses in the boss and engageable by the locking plunger 25. As shown the latter has a small diameter end portion 29 that registers with the balls 28 when the plunger 25 is in its withdrawn position as shown in the right-hand part of FIG. 1, permitting the balls 28 to enter the recesses sufficiently for them to become flush with the outer surface of the boss 22 and thus able to pass through a complementary bore in the upper end of the drive hub 10. Accordingly, with the locking plunger 25 withdrawn, the cover 12 may be removed from the drive hub 10 to give access to the interior of the head unit.

On the other hand, with the cover 12 in its closed position as shown on the left-hand side of FIG. 1, the locking plunger 25 may be pressed downwardly to cause its full diameter portion to register with the balls 28, forcing these outwardly in their recesses so as to engage the interior surface of the drive hub 10 and to lock the boss 22 against withdrawal from the latter, thereby securing the cover 12 in its closed position.

The bowl 11 is conveniently formed of aluminium or other light alloy sheet spun to the required shape whereas the cover 12 is conveniently of a transparent plastics material.

The carrier plate 13 has a central aperture that fits over the drive hub 10 and rests upon the upper surface of a flange at the lower end of the drive hub. Dowels (not shown) may be provided in this flange of the drive hub to mate with corresponding holes in the carrier plate 13 to locate this relative to the drive hub 10 and to avoid the risk of relative rotation between the hub and carrier plate during acceleration and deceleration of the motor 5 in operation of the machine.

The carrier plate is accordingly readily removable from the drive hub for cleansing and sterilization, as by autoclaving, when required.

The carrier plate is further formed with a series of symmetrically disposed apertures to receive a corresponding number of holder/sample chamber assemblies 14. The lateral boundaries of the apertures in the carrier plate 13 are formed with dependent flanges both to stiffen the carrier plate and to provide location for the assemblies 14, as will be explained.

The contruction and arrangement of each of the holder/sample chamber assemblies is best understood from FIGS. 2, 3 and 4. As shown in these Figures, the holder comprises a channel member 30 pressed from a stainless steel sheet so that it is of M-section, its web 31 joining its flanges 32 in reversely curved intermediate portions defining lateral ribs 33 along the rear or outer face of the web. These ribs provide additional stiffening for the web and also serve to stand-off a pivot rod 34 for a clamping element 35 and through the side cheeks 36 of which the pivot rod 34 passes to provide for rocking of the element 35, relatively to the channel member 30, about the axis defined by the pivot rod 34.

The lower end of the web of the channel member 30 is formed with a forwardly projecting lug 37 that serves to locate the lower ends of a microscope slide 38, a filter card 39 and a rectangular end flange 40 of a sample chamber unit consisting of a tubular sample chamber proper 41 the open end of which projects slightly beyond the corresponding face of the end flange 40 to provide an annular sealing surface 42 for engaging the filter 39; a funnel tube 43 leading to a lateral filling orifice 44 near the closed end of the chamber 41; and a support flange 45 that contains the axes of the chamber 41 and funnel tube 43 and extends perpendicularly from the front face of the end flange 40 along the longitudinal centerline thereof. The end flange 40, chamber 41, funnel tube 43 and flange 45 are preferably integrally formed by moulding a suitable plastics material.

The assembly of sample chamber unit, filter card 39 and slide 38 is held in the channel member of the holder by means of the clamping element 35. For this purpose the side cheeks 36 of the clamping element have inturned lugs 46 that overlie the flanges 32 of the channel member 30 in a position to engage the end flange 40 on opposite sides of the sample chamber 41 and approximately at the level of the center line thereof, when the bottom edge of the flange 40 is located in contact with the lug 37.

A hairpin spring 47 has its head engaged with the rear or outer face of the web 31 of the channel member 30 and its limbs wound about the pivot rod 34 so that its extremities engage the front or inner face of the element 35 and press thereon to rock this, relatively to the channel member 30, about the pivot rod 34 in the sense to cause the lugs 46 to press the flange 40 towards the web of the channel member and thereby to effect a seal between the open end of the sample chamber 41 and the slide 38 by pressing upon the interposed filter card 39.

In the embodiment described the hairpin spring 47 is designed to provide a clamping effort equivalent to a force of about 14 pounds (6.35 kg) applied through the lugs 46 to the flange 40.

The pivot rod 34 seats in depressions formed in the ribs 33 and is secured in position by extending through a hole in a tang 48 pressed out of the web 31 of the channel member 30. The pivot rod is further secured by wire clips 49 that pass around the pivot rod 34 and through the ribs 33 to have their extremities lying along the interior of the latter.

To enable the clamping force exerted by the spring 47 to be conveniently released and held while the sample chamber unit, slide and filter card are being placed in or removed from the holder, a release screw 50 is threaded into a boss 51 on the clamping element; by screwing the screw 50 through the boss 51 and so that its leading end engages the rear (outer) face of the web 31 of the channel member, the clamping element 35 is caused to rock about the pivot rod 34 in opposition to the torsion of the spring 47.

In order to expose the surface of the slide 38 to the sample chamber 41, the filter card 39 is provided with a hole corresponding in size with the bore of the chamber 41 and positioned so as to be concentric with the chamber 41 when the lower end of the filter card is coextensive with the lower end of the flange 40—i.e. the relationship achieved when the flange 40 and filter 39 are both engaged with the lug 37.

The embodiment being described is intended to utilize standard microscope slides as the slides 38 and filter cards 39 having a corresponding dimension and as are available on the market for use in existing cytocentrifuge apparatus. Such filter cards have two holes therein equidistant from the respective ends of the card and so positioned that one or the other will be aligned with the sample chamber regardless of which end of the filter card is registered with the lower edge of the flange 40. To facilitate this registration of the filter card with the end flange 40, the latter is preferably provided with a projection (not shown) positioned to engage in the unused hole in the filter card when this is correctly registered with the end flange 40 to align the other hole in the card with the sample chamber.

The dimensions of the sample chamber 41 are selected to provide a suitable volume to contain a sample of a desired magnitude, for instance 0.5 ml, and to hold such sample with its surface below the lowest point of the open end of the sample chamber when the latter is tilted a few degrees, e.g. 13 degrees, out of the horizontal.

Each of the described holder/sample chamber assemblies 14 is arranged to seat in an aperture in the carrier plate 13 with the extremities of its pivot rod 34 resting in notches formed in flanges 52 bounding the edges of the carrier plate aperture. The arrangement is such that when the carrier plate is at rest so that only gravitational forces act upon the holder/sample chamber assembly, the latter rocks about the pivot rod 34 to the position indicated in broken lines in FIGS. 1 and 2, whereby the axis of the sample chamber 41 is tilted downwardly and inwardly at a small angle of, conveniently, about 13 degrees in the case of the illustrated embodiment. This tilting of the assembly under gravitational forces is limited by engagement of the flange 45 with the inner edge of the associated aperture in the carrier plate.

However, when the carrier plate is rotated by rotation of the drive hub 10 by the motor 5, centrifugal forces acting on the assemblies 14 cause each of these to tilt outwardly about its pivot rod 34 to adopt the upright position shown in full lines in FIGS. 1 and 2 and in which the axis of the sample chamber 41 is horizontal and perpendicular to the axis of rotation, and the slide 38 is accordingly vertical and perpendicular to the centrifugal force acting on the contents of the sample chamber 41. Thus during centrifugation, the sample contained within a sample chamber 41 is uniformly and symmetrically thrust against the exposed inner receiving surface of the slide 38 so that cells and other solids suspended in the fluid of the sample are uniformly and symmetrically deposited on the exposed slide surface. The liquid contents of the sample chamber under these conditions are caused to flow in the filter card, uniformly and symmetrically away from the inner periphery of the aperture in the filter card defining the junction between the sample chamber bore and the receiving surface of the slide 38.

It will thus be apparent that the cytocentrifuge construction described provides for delayed contact between the sample fluid and the receiving surface and filter until the commencement of centrifugation, and thereafter for the uniform deposition and symmetrical filtration of the constituents of the sample fluid. It will also be apparent that the head unit provides sealed containment of the materials being centrifuged and that is readily detachable for separate transport to a suitable containment zone for opening and handling of its contents within such a zone.

Furthermore the construction of the holders and of the removable carrier plate enables these likely-to-be-contaminated components to be readily cleansed and sterilized as required and for the centrifuge to be operated continuously by the use of exchangeable holder/sample chamber assemblies and, if desired, exchangeable carrier plates, in a single head unit.

What is claimed is:

1. A cytocentrifuge comprising
   (a) a rotating carrier; and
   (b) a plurality of assemblies mounted on the carrier for rotation therewith and for removal therefrom as a unit, each assembly including
      (1) a holder comprising a channel member having a web and a flange, the channel member retaining a slide providing a receiving surface and a filter card overlying the slide and providing an absorbent seal thereover,
      (2) a sample chamber comprising a tube having an end flange shaped to be received by the holder in overlying relationship to the slide and filter card; and
      (3) said holder further comprising clamping means adapted to engage the end flange of the sample chamber for urging the same towards the web of the channel member whereby the assembly of sample chamber, filter card and slide is secured.

2. The cytocentrifuge of claim 1 in which each said assembly is adapted to be supported by the rotating carrier in a manner permitting tilting of the asssembly about a horizontal axis in response to gravitational and centrifugal loads whereby when the carrier is at rest the assembly adopts a position in which the axis of the sample chamber is inclined downwardly and inwardly of the carrier, whereas under the centrifugal loads arising from rotation of the carrier, the assembly tilts to a position in which the sample chamber axis is horizontal and perpendicular to the axis of rotation.

3. A cytocentrifuge comprising
   (a) a rotating carrier; and
   (b) a plurality of assemblies mounted on the carrier for rotation therewith and for removal therefrom as a unit, each assembly including
      (1) a holder comprising a channel member having a web and a flange, the channel member retaining a slide providing a receiving surface and a filter card overlying the slide and providing an absorbent seal thereover,
      (2) a sample chamber comprising a tube having an end flange shaped to be received by the holder in overlying relationship to the slide and filter card; and
      (3) said holder further comprising clamping means adapted to engage the end flange of the sample chamber for urging the same towards the web of the channel member whereby the assembly of sample chamber, filter card and slide is secured, the clamping means comprising
      (4) a rocking element pivoted to the channel member, the channel member having two of said flanges and the rocking element having lugs extending over the flanges of the channel member to engage the end flange of the sample chamber, the rocking member being spring-loaded for rocking in a direction causing the lugs to move towards the web of the channel member whereby a clamping force is produced on the end flange of the sample chamber.

4. The cytocentrifuge of claim 3 in which said rocking element carries a release screw that may be manipulated first to engage the outer face of the channel member web and thereafter forcibly to rock the rocking element in the clamp-releasing direction and to hold the rocking element in a clmap-released position to facilitate assembly and disassembly of the sample chamber, filter card and slide in the holder.

5. The cytocentrifuge of claim 3 in which said holder channel has lateral stiffening ribs along its rear or outer aspect, these ribs being recessed to provide locations for a pivot rod that extends across such ribs and through a rearwardly directed tang pressed out of the web, this pivot rod extending through side cheeks in the rocking element and carrying a hairpin spring acting respectively on the rear face of the holder web and upon the rocking element to tend to rotate the latter about the pivot rod.

6. The cytocentrifuge of claim 3 in which said lugs of the rocking element are positioned to engage the end flange of the sample chamber adjacent to a diameter of the latter.

7. The cytocentrifuge of claim 3 in which said holder channel member has an end stop at one end to locate the components in the required mutual relationship with one another and with the holder, the other end of the channel member being open to permit the components to be slid out of the channel member upon release of the said clamping means.

8. The cytocentrifuge of claim 3 in which each said sample chamber comprises a tube having one end integrally formed with a rectangular end flange, and a lateral filling orifice near its other end.

9. The cytocentrifuge of claim 8 including a funnel tube communicating with said filling orifice.

10. The cytocentrifuge of claim 9 in which said funnel tube is integrally formed with the sample chamber and also with lateral flanges that extend to join the end flange of the sample chamber along the longitudinal centerline of the end flange.

11. The cytocentrifuge of claim 3 in which the rotating carrier is formed as a plate with apertures to receive the assemblies and a central aperture to fit over a drive hub from which the carrier pate may be removed at will for cleansing and sterilization as required.

12. The cytocentrifuge of claim 12 including a containment bowl and removable cover carried by said drive hub and constituting a sealable head assembly that may be removed as a unit from the machine to permit of its being handled in a containment zone.

13. The cytocentrifuge of claim 11 in which said drive hub is formed with an internal tapered drive surface for mating with a complementarily tapered driving element on a vertical drive shaft.

* * * * *